US010954481B2

(12) United States Patent
Ku

(10) Patent No.: US 10,954,481 B2
(45) Date of Patent: Mar. 23, 2021

(54) PILLAR UNIT FOR BIO CHIP

(71) Applicant: MBD CO., LTD., Suwon-si (KR)

(72) Inventor: Bosung Ku, Yongin-si (KR)

(73) Assignee: MBD CO., LTD., Suwon-si (KR)

( * ) Notice: Subject to any disclaimer, the term of this patent is extended or adjusted under 35 U.S.C. 154(b) by 87 days.

(21) Appl. No.: 16/132,006

(22) Filed: Sep. 14, 2018

(65) Prior Publication Data

US 2019/0233789 A1     Aug. 1, 2019

(30) Foreign Application Priority Data

Jan. 30, 2018   (KR) .......................... 10-2018-0011404

(51) Int. Cl.
  *C12M 1/32*      (2006.01)
  *G01N 33/53*    (2006.01)
  (Continued)

(52) U.S. Cl.
  CPC ........... *C12M 23/12* (2013.01); *B01L 3/5085* (2013.01); *B01L 3/50853* (2013.01);
  (Continued)

(58) Field of Classification Search
  CPC ...... C12M 23/12; C12M 23/42; C12M 23/44; C12M 31/02; C12M 25/06; C12M 1/3446; B01L 2300/0819; B01L 2300/0803; B01L 2300/1805; B01L 2300/1861; B01L 2300/041; B01L 23/0829; B01L 9/52; B01L 3/50851; B01L 3/50853; B01L 3/5085; B01L 2200/028; B01L 2200/025; B01L 2300/0893; B01L 2200/10; B01L 2300/0848; B01L 9/523; B01L 2200/0689; C12Q 1/6883; C12Q 1/6827;
  (Continued)

(56) References Cited

U.S. PATENT DOCUMENTS

| 2003/0215940 A1* | 11/2003 | Lacey | .................... C12M 23/12 |
| | | | 435/305.2 |
| 2007/0082390 A1* | 4/2007 | Hastings | ............... B01L 3/5085 |
| | | | 435/305.2 |
| 2019/0134625 A1* | 5/2019 | Ku | ...................... B01L 3/50853 |

FOREIGN PATENT DOCUMENTS

KR      10-2014-0073139 A      6/2014
KR         20170106169 A   *   9/2017

OTHER PUBLICATIONS

Machine English Translation (Year: 2017).*

* cited by examiner

*Primary Examiner* — Michael L Hobbs
*Assistant Examiner* — Lenora A Abel
(74) *Attorney, Agent, or Firm* — Birch, Stewart, Kolasch & Birch, LLP

(57) ABSTRACT

A pillar unit for a bio chip can include a plate-form substrate having a plurality of holder parts, which are spaced apart from each other, and each of the plurality of holder parts includes a holding space, to which a pillar is inserted and fixed, in which each of the plurality of holder parts further includes a pair transformation slits so that the corresponding holder part may be transformed and restored while the pillar is accommodated in the holding space; and a plurality of pillars corresponding to the plurality of holder parts, each of the plurality of pillars is accommodated in the holding space in one of the plurality of holder parts, one end of each of the plurality of pillars is combined with one holder part among the plurality of holder parts and is detachable, and the other end of each of the pillars includes a sample.

12 Claims, 5 Drawing Sheets

(51) Int. Cl.
  *B01L 3/00*    (2006.01)
  *C12M 3/00*    (2006.01)
  *C12M 1/12*    (2006.01)
  *C12M 1/00*    (2006.01)

(52) U.S. Cl.
  CPC ............ *C12M 23/42* (2013.01); *C12M 23/44* (2013.01); *C12M 25/06* (2013.01); *C12M 31/02* (2013.01); *G01N 33/5302* (2013.01); *B01L 2200/025* (2013.01); *B01L 2200/028* (2013.01); *B01L 2200/10* (2013.01); *B01L 2300/046* (2013.01); *B01L 2300/0819* (2013.01); *B01L 2300/0829* (2013.01); *B01L 2300/0893* (2013.01)

(58) Field of Classification Search
  CPC ...... C12Q 1/6816; C12Q 1/6869; C12Q 1/04; C12Q 2600/156; G01N 33/54366; G01N 33/54373; G01N 27/26; G01N 33/48; G01N 33/5302; G01N 21/6428; G01N 21/6452; G01N 21/253; G01N 35/025; G01N 2035/00366; B01J 2219/00722; B01J 19/0046; B82Y 30/00; B01N 21/00
  USPC ...................................................... 435/305.2
  See application file for complete search history.

[Figure 1]      ------------ Prior Art -----------
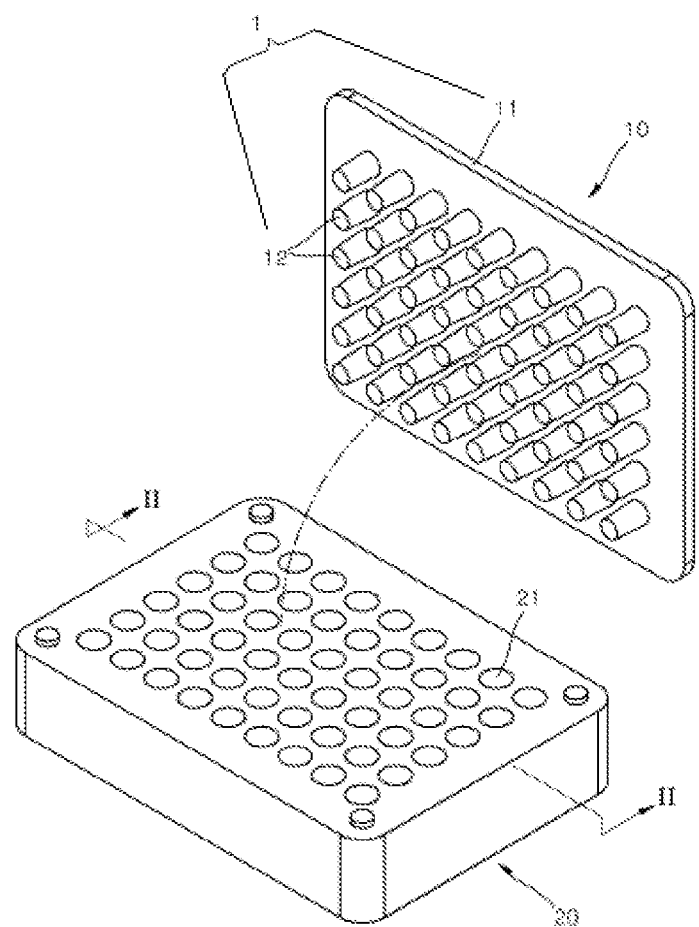

[Figure 2]  ------------ Prior Art -----------
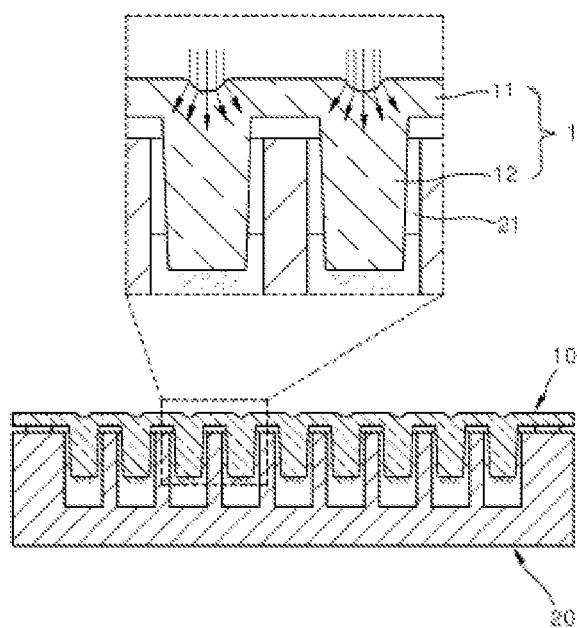

[Figure 3]
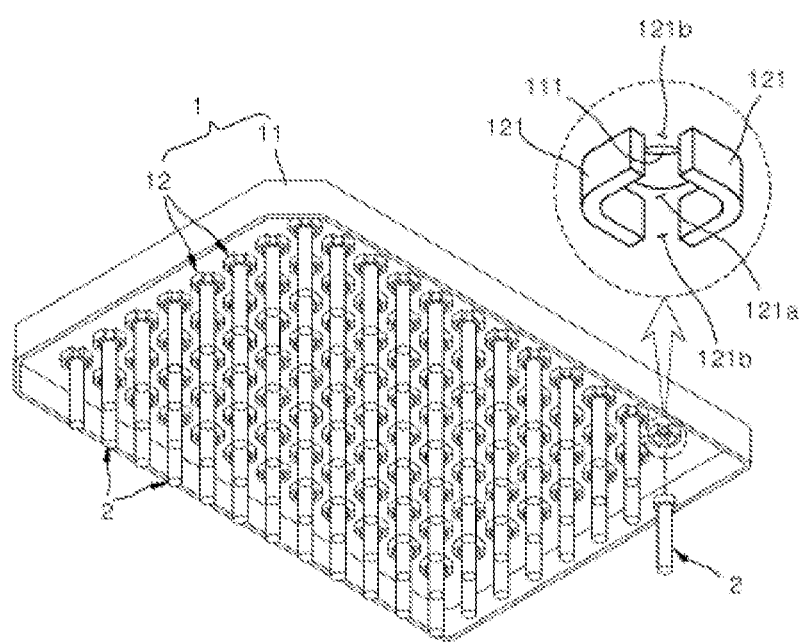

[Figure 4]
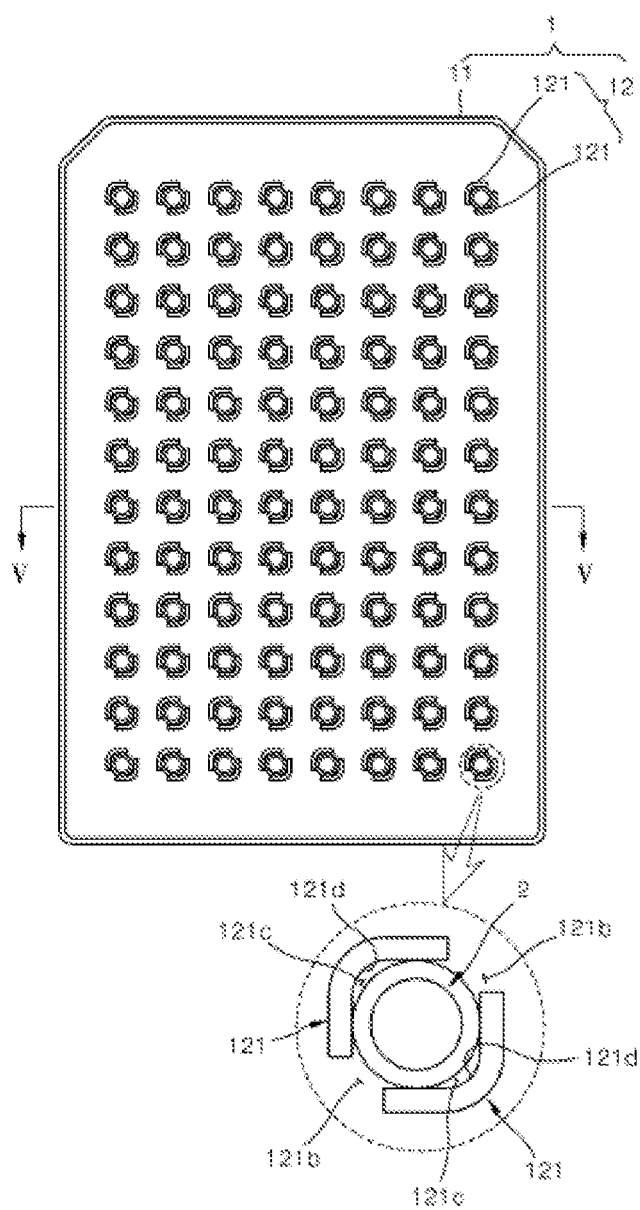

[Figure 5]
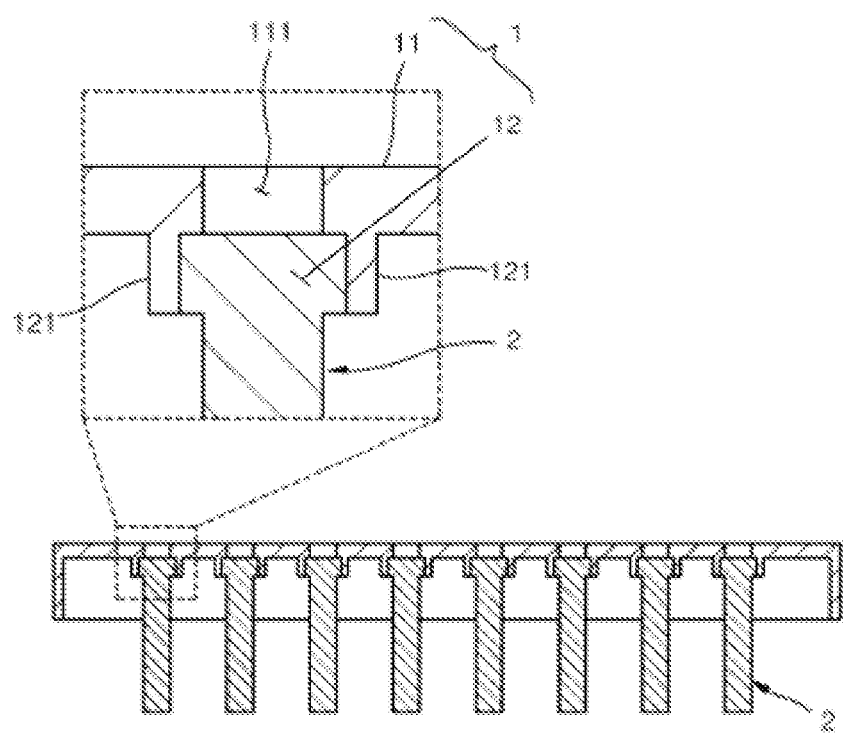

PILLAR UNIT FOR BIO CHIP

CROSS-REFERENCE TO RELATED PATENT APPLICATION

This application claims the benefit of Korean Patent Application No. 10-2018-0011404, filed on Jan. 30, 2018, in the Korean Intellectual Property Office, the disclosure of which is incorporated herein in its entirety by reference.

BACKGROUND OF THE INVENTION

1. Field of the Invention

The present invention relates to a pillar unit for a bio chip, and more particularly, to a pillar unit for a bio chip having an improved structure so that pillars, where samples to be analyzed are attached, may be easily combined with and separated from a substrate and light transmittance of a light source radiated to the sample may increase for analyzing the sample.

2. Description of the Related Art

A bio chip is a bio device or a bio element and is a biological microchip in which samples of biological micro-substances such as DNA, protein, and cells are disposed on a substrate and are analyzed in terms of genetic defect, protein distribution, and responses. Such a bio chip is widely used in areas such as a scientific technique research, a drug development process, and a clinical diagnosis.

In general, a bio chip includes a pillar plate 10 and a well plate 20, as illustrated in FIGS. 1 and 2. FIG. 1 is a perspective view of a conventional bio chip and FIG. 2 is a cross-sectional view of the bio chip of FIG. 1 cutting along II-II.

As illustrated in FIGS. 1 and 2, the pillar plate 10 of the conventional bio chip includes a substrate 1 and protruding pillar-formed pillar units 12 on one surface of the substrate 1 as one body. The well plate 20 includes a plurality of well units 21 where the pillar units 12 are accommodated.

The pillar units 12 formed as one body with the substrate 1 include samples at the end parts thereof and a culture medium is accommodated in the well units 21. In such a conventional bio chip, the pillar plate 10 is disposed on the well plate 20 so that the well units 21, where a culture medium is included, may accommodate the samples disposed in the pillar units 12. Also, the bio chip enables a microscope to check the samples using the pillar units 12 through which a light source penetrates (refer to FIG. 2).

Since the conventional bio chip illustrated in FIGS. 1 and 2 is manufactured by injection molding, the pillar units 12 and the substrate 1 are formed to be one body.

In such conventional bio chip, since all samples have to be analyzed at the same time at fixed pillar intervals, a customized analysis by placing a relatively small number of samples at wider intervals or by placing a large number of samples at narrow intervals may not be possible. Also, when samples are not properly attached to some pillar units and thus a correction is needed or when the pillar units need to be partly detached for more detailed analysis after analyzing, the whole pillar plate is handled instead of separately handling the pillar units.

SUMMARY OF THE INVENTION

The present invention provides a pillar unit for a bio chip in which pillars, where samples to be analyzed are attached, may be easily combined with and separated from a substrate.

The present invention also provides a pillar unit for a bio chip by which light transmittance of a light source radiated to the sample may increase for analyzing the sample.

According to an aspect of the present invention, there is provided a pillar unit for a bio chip for forming a bio chip along with a well plate, in which a culture medium is accommodated, wherein the bio chip analyzes samples of biological micro-substances such as cells, the pillar unit may include: a plate-form substrate comprising a plurality of holder parts, which is spaced apart from each other, arranged vertically and horizontally, and comprises a holding space, to which an object is inserted and fixed, wherein each of the holder parts comprises transformation slits so that the holder part may be transformed and restored while the object is accommodated in the holding space; and a plurality of pillars corresponding to the above object which is accommodated in the holding space of the substrate, wherein one end of the pillar is combined with each holder part and is detachable, and the other end of the pillar includes the sample.

The holder part of the substrate may include a pair of transformation ribs which is spaced apart from each other by placing the pillar therebetween to form the holding space and the pair of transformation slits.

The pair of transformation ribs may include non-contact surfaces forming non-contact grooves, where the pillar does not contact.

The substrate may include a plurality of penetration holes at positions corresponding to the holder parts so that a light source may be smoothly radiated to the upper surfaces of the pillars inserted into the holder parts.

BRIEF DESCRIPTION OF THE DRAWINGS

The above and other features and advantages of the present invention will become more apparent by describing in detail exemplary embodiments thereof with reference to the attached drawings in which:

FIG. 1 is a perspective view of a conventional bio chip;

FIG. 2 is a cross-sectional view of the bio chip of FIG. 1 cutting along II-II;

FIG. 3 is a perspective view of a pillar unit for a bio chip according to an embodiment of the present invention;

FIG. 4 is a bottom view of the pillar unit of FIG. 3; and

FIG. 5 is a cross-sectional view of the pillar unit of FIG. 3 cutting along V-V of FIG. 4.

DETAILED DESCRIPTION OF THE INVENTION

Hereinafter, a pillar unit for a bio chip according to an embodiment of the present invention will be described more fully with reference to the accompanying drawings.

FIG. 3 is a perspective view of a pillar unit for a bio chip according to an embodiment of the present invention, FIG. 4 is a bottom view of the pillar unit of FIG. 3; and FIG. 5 is a cross-sectional view of the pillar unit of FIG. 3 cutting along V-V of FIG. 4.

As illustrated in the drawings above, the pillar unit for a bio chip according to an embodiment of the present invention is used to form a bio chip along with a well plate, in which a culture medium is accommodated, wherein the bio chip analyzes samples of biological micro-substances such as cells. The pillar unit is individually produced and includes a substrate 1 and pillars 2, both of which may be attached and detached.

As illustrated in FIG. 3, the substrate 1 includes a flat plate-form main body part 11 and a plurality of holder parts 12 which is formed as one body with the main body part 11, disposed on the lower surface of the main body part 11, spaced apart from each other, and arranged vertically and horizontally.

Each of the holder parts 12 includes a holding space 121a, to which an object is inserted and fixed, and a transformation slit 121b to transform the holding space 121a.

That is, the transformation slit 121b transforms the holder part 12 while an object approaches the holding space 121a and thus makes a smooth combination between the object and the holder part 12. When the object is accommodated in the holding space 121a, the transformation slit 121b restores a shape of the holder part 12 so that the object may be tightly fixed to the holder part 12.

The pillar 2 corresponds to the above object which is accommodated in the holding space 121a of the substrate 1. The one end of the pillar 12 is combined with each holder part 12, wherein the pillar 12 may be detached, and the other end of the pillar 12 includes the sample. Here, the 'detached' means that the object may be combined and separated by its own structure without using other combining means.

Such pillar unit for a bio chip according to an embodiment of the present invention is formed so that the substrate 1 and the plurality of pillars 2 are easily combined with each other and separated through the holder parts 12 including the transformation slit 121b. Accordingly, the pillars 2 may be individually separated from the substrate 1, if needed, and thus a customized analysis on the sample may be possible. Therefore, the efficiency of analysis and users' convenience may improve.

The holder part 12 according to an embodiment of the present invention includes a pair of transformation ribs 121 which is spaced apart from each other by placing the pillar 2 therebetween to form the holding space 121a and the pair of transformation slits 121b. That is, each of the transformation slits 121b is formed between end parts of the transformation ribs 121, which face each other, and enables the shape of the holder part 12 to transform and restore.

In addition, the pair of transformation ribs 121 includes non-contact surfaces 121d forming non-contact grooves 121c, where the pillar 2 does not contact, as illustrated in FIG. 4.

That is, when the pillar 2 is accommodated in the holding space 121a of the holder part 12, each of the transformation ribs 121 includes the non-contact surfaces 121d, where the pillar 2 does not contact, and thus a contact surface of the pillar 2 in the holder part 12 may be minimized. As a result, the efficiency of the combination and separation between the holder part 12 and the pillar 2 may improve.

As illustrated in FIG. 5, the main body part 11 of the substrate 1 according to an embodiment of the present invention includes a plurality of penetration holes (111) at positions corresponding to the holder parts 12 so that a light source may be smoothly radiated to the upper surfaces of the pillars 2 inserted into the holder parts 12.

That is, when a light source used to analyze the sample passes through the substrate 1 and is radiated to the pillar 2, the substrate 1 according to an embodiment of the present invention includes the penetration holes (111) and thereby, a light may be radiated straight to the pillar 2 instead of being curved or reflected after the light passes the medium. Therefore, accuracy of sample analysis using a light source may improve.

In addition, since a light source has to pass a medium such as upper plate of the substrate 1 in the conventional art, the substrate 1 needs to be formed using a resin, by which a light may penetrate. However, the substrate 1 according to an embodiment of the present invention includes the penetration holes (111), through which a light source may pass without a medium, and thus the substrate 1 may be formed using not only a resin but also a metal material, by which a light does not penetrate.

The pillar unit for a bio chip described above according to the present invention is formed for the substrate and the plurality of pillars to be easily combined with each other and separated through the holder parts including the transformation slits. Accordingly, the pillars may be individually separated from the substrate, if needed, and thus a customized analysis on the sample may be possible. Therefore, the efficiency of analysis and users' convenience may improve.

Also, in the embodiment describing forming the penetration holes, where a light source penetrates, on the substrate, when a light source used to analyze the sample passes through the substrate and is radiated to the pillar, a light may be radiated straight to the pillar instead of being curved or reflected after the light passes the medium. Therefore, accuracy of sample analysis using a light source may improve.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A pillar unit for a bio chip for forming a bio chip along with a well plate, in which a culture medium is accommodated, the pillar unit comprising:
   a plate-form substrate comprising a plurality of holder parts, which are spaced apart from each other,
   wherein each of the plurality of holder parts comprises a holding space, to which a pillar is inserted and fixed, and
   wherein each of the plurality of holder parts further comprises a pair transformation slits so that the corresponding holder part may be transformed and restored while the pillar is accommodated in the holding space; and
   a plurality of pillars corresponding to the plurality of holder parts,
   wherein each of the plurality of pillars is accommodated in the holding space in one of the plurality of holder parts,
   wherein one end of each of the plurality of pillars is combined with one holder part among the plurality of holder parts and is detachable, and the other end of each of the plurality of pillars includes a sample,
   wherein the plate-form substrate further comprises a plurality of penetration holes at positions corresponding to the plurality of holder parts so that a light can be transmitted through each of the plurality of pillars and radiated to the sample on upper surfaces of the plurality of pillars inserted into the plurality of holder parts,
   wherein each of the plurality of holder parts in the plate from substrate comprises a pair of transformation ribs which are spaced apart from each other by placing a corresponding pillar among the plurality of pillars therebetween to form the holding space and the pair of transformation slits,
   wherein the pair of transformation ribs comprises non-contact surfaces forming non-contact grooves, where the corresponding pillar does not contact, and wherein the pair of transformation slits transforms the corresponding holder part while the corresponding pillar approaches the holding space and thus makes a smooth combination between the corresponding pillar and the corresponding holder part, and when the corresponding pillar is accommodated in the holding space, the pair of transformation silts restore a shape of the corresponding holder part so that the corresponding pillar may be tightly fixed to the corresponding holder part.

2. The pillar unit according to claim 1, wherein each transformation rib among the pair of transformation ribs includes two straight portions and a curved portion between the two straight portions, the curved portion forming one of the non-contact grooves.

3. The pillar unit according to claim 2, wherein the corresponding pillar contacts the two straight portions.

4. A pillar unit for a bio chip, the pillar unit comprising:
a plurality of holder parts disposed on a plate-form substrate; and
a plurality of detachable pillars disposed in the plurality of holder parts, respectively,
wherein each of the plurality of holder parts includes a pair of transformation slits, a pair of transformation ribs and a holding space located between the pair of transformation ribs,
wherein the pair of transformation ribs are configured to flex into a holding shape when receiving a corresponding detachable pillar from among the plurality of detachable pillars, and
wherein each transformation rib among the pair of transformation ribs includes two straight portions and a curved portion between the two straight portions, the curved portion forming a non-contact groove that does not contact the corresponding detachable pillar when the pair of transformation ribs are in the holding shape, and each transformation rib among the pair of transformation ribs has a length relative to a surface of the plate-form substrate that is less than half of a length of the corresponding detachable pillar relative to the surface of the plate-form substrate.

5. The pillar unit according to claim 4, wherein the plate-form substrate includes a plurality of penetration holes penetrating through opposite sides of the plate-form substrate, and
wherein each of the plurality of penetration holes overlaps with a center of one of the plurality of pillars.

6. The pillar unit according to claim 5, wherein each of the plurality of penetration holes overlaps with the holding space located between the pair of transformation ribs.

7. The pillar unit according to claim 4, wherein the pair of transformation ribs are configured to transform into a restored shape from a holding shape when the corresponding detachable pillar is removed from the holding space, and
wherein the restored shape is different from the holding shape.

8. The pillar unit according to claim 4, pair of transformation ribs have mirror symmetry relative to an imaginary line extending through a center point between the pair of transformation ribs.

9. The pillar unit according to claim 4, wherein each of the plurality of pillars is made of a transparent material.

10. The pillar unit according to claim 4, wherein each of the plurality of pillars has a peg shape or a cylinder shape.

11. The pillar unit according to claim 4, wherein each of plurality of pillars has a long side and a short side shorter than the long side, and
wherein the long side is disposed perpendicular to the plate-form substrate.

12. The pillar unit according to claim 4, wherein the corresponding detachable pillar is held between the pair of transformation ribs by a friction fit when the pair of transformation ribs are in the holding state.

* * * * *